(12) United States Patent
Liberman et al.

(10) Patent No.: US 7,253,175 B2
(45) Date of Patent: Aug. 7, 2007

(54) METHOD FOR TREATING ATHLETE'S FOOT

(76) Inventors: Barnet Liberman, 421 Hudson St., New York, NY (US) 10014; Albert Lefkovits, 715 Park Ave., New York, NY (US) 10021

( * ) Notice: Subject to any disclaimer, the term of this patent is extended or adjusted under 35 U.S.C. 154(b) by 817 days.

(21) Appl. No.: 10/712,514

(22) Filed: Nov. 13, 2003

(65) Prior Publication Data

US 2005/0107407 A1   May 19, 2005

(51) Int. Cl.
*A61K 31/52* (2006.01)
*A61K 31/522* (2006.01)
*A01N 43/90* (2006.01)

(52) U.S. Cl. .............. 514/263.1; 514/263.3; 514/263.4

(58) Field of Classification Search ............ 514/263.1, 514/263.3, 263.4
See application file for complete search history.

(56) References Cited

U.S. PATENT DOCUMENTS

| 4,199,574 | A | | 4/1980 | Schaeffer | |
|---|---|---|---|---|---|
| 4,957,924 | A | | 9/1990 | Beauchamp | |
| 5,246,937 | A | | 9/1993 | Harnden et al. | |
| 5,519,059 | A | * | 5/1996 | Sawaya | 514/599 |
| 6,224,887 | B1 | * | 5/2001 | Samour et al. | 424/401 |
| 6,258,831 | B1 | | 7/2001 | Camden | |
| 6,436,926 | B1 | * | 8/2002 | Costin | 514/222.5 |
| 6,585,967 | B2 | * | 7/2003 | Narang et al. | 424/78.31 |
| 6,951,847 | B2 | * | 10/2005 | Gibson et al. | 514/169 |

OTHER PUBLICATIONS

PCT International Search Report PCT/US04/27175, Aug. 20, 2004, Liberman, Barnet.

* cited by examiner

*Primary Examiner*—Alton Pryor
(74) *Attorney, Agent, or Firm*—Cohen Pontani Lieberman & Pavane LLP

(57) ABSTRACT

A method of treating a patient having a fungal infection comprises administering an effective fungal infection treatment amount of an antiviral agent, such as valacyclovir, to eliminate the symptoms of the fungal infection.

9 Claims, No Drawings

METHOD FOR TREATING ATHLETE'S FOOT

BACKGROUND OF THE INVENTION

1. Field of the Invention

The present invention is directed to a method of treating a fungal infection, such as athlete's foot, by orally or topically administrating an antiviral agent, such as valacyclovir hydrochloride, acyclovir and famcyclovir to patients suffering from such fungal infection.

2. Description of the Related Art

Athlete's foot is a skin disease, usually occurring between the toes, which is believed currently caused by a fungus. The fungus most commonly attacks the feet because shoes create a warm, dark, and humid environment which encourages fungus growth. The warmth and dampness of areas around swimming pools, showers, and locker rooms, are also breeding grounds for fungi. Because the infection was common among athletes who used these facilities frequently, the term "athlete's foot" became popular. Not all fungus conditions are athlete's foot. Other conditions, such as disturbances of the sweat mechanism, reaction to dyes or adhesives in shoes, eczema, and psoriasis, also may mimic athlete's foot.

The signs of athlete's foot, singly or combined, are itching scaling skin, often accompanied by inflammation, by blisters. Blisters often lead to cracking of the skin. When blisters break, small raw areas of tissue may be exposed, possibly causing pain and swelling. Itching and burning may increase as the infection spreads.

Athlete's foot may invade to the soles of the feet in between the toes and the toenails. It can also be spread to other parts of the body, notably the groin and underarms, by those who scratch the infection and then touch themselves elsewhere. The organisms causing athlete's foot may persist for long periods.

Fungal infection of toenails is a common foot health problem. A majority of victims do not seek treatment or may not even recognize the existence of a problem. Probably because the infection can be present for years without ever causing pain. Its prevalence rises sharply among older adults. Studies estimate that it afflicts three to five percent of the population. However, doctors of podiatric medicine believe that because so many cases go unreported, the incidence may be four times higher than what have been reported. They estimate that about 10 million people are infected annually.

Fungi are simple parasitic plant organisms, such as molds and mildew, that lack chlorophyll and therefore do not require sunlight for growth. A group of fungi called dermatophytes easily attack the nail, thriving off keratin, the nail's protein substance. Fungal infection of the nails is known to Physicians and other physicians as onychomycosis. It is an infection underneath the surface of the nail, which can also penetrate the nail. Onychomycosis is caused by various types of fungi, which are commonly found throughout the environment.

When the tiny organisms take hold, the nail may become thicker, yellowish-brown or darker in color, and foul smelling. Debris may collect beneath the nail plate, white marks frequently appear on the nail plate, and the infection is capable of spreading to other toenails, the skin, or even the fingernails.

Because it is difficult to avoid contact with microscopic organisms like fungi, the toenails are especially vulnerable around damp areas where people are likely to be walking barefoot—swimming pools, locker rooms, and showers, for example. Injury to the nail bed may make it more susceptible to all types of infection, including fungal infection. Those who suffer chronic diseases, such as diabetes, circulatory problems, or immune-deficiency conditions, are especially prone to fungal nails. Other contributory factors may be a history of athlete's foot and excessive perspiration.

The disease, characterized by a change in a toenail's color, is often considered nothing more than a mere blemish—ugly and embarrassing. In many cases, however, that change in color is the start of an aggravating disease that ultimately could take months to control. If it is ignored, its spread could impair one's ability to work or even walk. That happens because it is frequently accompanied by thickening of the nails, which then cannot easily be trimmed and may cause pain while wearing shoes. This disease can frequently be accompanied by a secondary bacterial and/or yeast infection in or about the nail plate.

It is not easy to prevent athlete's foot because it is usually contracted in dressing rooms, showers, and swimming pool locker rooms where bare feet come in contact with the fungus. Fungicidal and fungistatic chemicals, used for athlete's foot treatment, frequently fail to contact the fungi in the horny layers of the skin.

Physicians can detect a fungal infection early, culture the nail, determine the cause, and form a suitable treatment plan, which may include prescribing topical or oral medication, and debridement (removal of diseased nail matter and debris) of an infected nail. Indeed, debridement is one of the most common foot care procedures performed by DPMs.

If a Physician determines a fungus is the cause of the problem, a specific treatment plan, including the prescription of antifungal medication, applied topically or taken by mouth, will usually be suggested. If there is a secondary infection caused by bacteria, antibiotics, such as penicillin, may be prescribed. Depending on the nature of the infection and the severity of each case, treatment may vary.

However, even the best counter treatments may not prevent a fungal infection from coming back. A fungus may work its way through the entire nail, penetrating both the nail plate and the nail bed. If an infection is not overcome, or continues to reappear, further medical attention will be necessary.

Newer oral antifungals such as lamisil approved by the Food and Drug Administration such as lausid spervenoy, may be the most effective treatment. They offer a shorter treatment outlook (three to four months) and improved effectiveness, though physicians advise that lengthier treatments, up to 12 months, may still be required for some infections. Current studies show that, for a small percentage of the population, there are some unwanted side effects caused by any oral antifungal.

The commercially available anti-viral agents, such as acyclovir, valacyclovir, famciclovir, and ganciclovir, combat against human herpes virus mainly by inhibiting viral replication. Acyclovir has proven to be specifically effective against herpes simplex (HSV) 1 and 2 and herpes zoster. Acyclovir is a guanosine analog with an acyclic side chain at the 9 position. Acyclovir selectively acts against human herpes viruses, including HSV-1/-2, varicella zoster virus (VZV), Epstein-Barr virus (EBV) and cytomegalovirus (CMV) through several enzymatic reactions, each of which is unique to virus replication: specific activation (phosphorylation) by a virus-induced thymidine kinase (TK); selective inhibition of the viral DNA polymerase by acyclovir di- and triphosphate (ACVTP) acting as a competitor with the natural substrate, dGTP; termination of viral DNA chain growth by incorporation of acyclovir monophosphate (ACVMP); and inactivation of the viral DNA polymerase following ACVMP incorporation in the presence of dNTPs. More specifically, acyclovir is transported into cells by the nucleoside transporter which also transports guanine. It requires a virus-encoded TK for efficient intracellular activation which accounts, in part, for its selectivity.

Valacyclovir, valine ester of acyclovir, is one of a number of oral acyclocvir prodrugs which lead to higher blood levels than the parent compound. Valacyclovir turns into acyclovir in the patient's body after administration. It functions against human herpes viruses through the same mechanism as acyclovir.

Valacyclovir hydrochloride (tradename Valtrex) is the hydrochloride salt of L-valyl ester of acyclovir. The chemical name of valacyclovir hydrochloride is L-valine, 2-[(2-amino-1,6-dihydro-6-oxo-9H-purin-9-yl)methoxy]ethyl ester, monhydrochloride. After oral administration, valacyclovir is rapidly and almost completely converted to acyclovir and L-valine, a naturally occurring amino acid.

Famciclovir, a prodrug of penciclovir, is related to acyclovir but its activated triphosphate form has a much lower intracellular half-life than ACVTP. Penciclovir triphosphate has a hydroxy group at a position corresponding to the 3' hydroxyl of the 2,-deoxyribose ring, although it is not an obligate chain-terminator, it inhibits DNA polymerization and virus replication. Since penciclovir itself has poor oral bioavailability, famciclovir was developed which is a diester prodrug with good absorption properties.

Ganciclovir is an acyclic nucleoside analogue of 2'-deoxyguanosine that inhibits replication of herpes viruses. Ganciclovir triphosphate is believed to inhibit viral DNA synthesis by (1) competitive inhibition of viral DNA polymerases; and (2) incorporation into viral DNA, resulting in eventual termination of viral DNA elongation.

Penciclovir is known as 9-[4-hydroxy-3-(hydroxymethyl) butyl]guanine. It has inhibitory activity against herpes simplex virus types 1 (HSV 1) and 2 (HSV 2). In vitro studies demonstrate that penciclovir triphosphate inhibits HSV polymerase competitively with deoxyguanosine triphosphate. Consequently, herpes viral DNA synthesis and, therefore, replication are selectively inhibited. In cell culture, penciclovir exhibits antiviral activity against HSV-1 and HSV-2.

Insofar as applicants know, the above described antiviral drugs have never been used to treat athlete's foot or any fungus infections.

SUMMARY OF THE INVENTION

An object of the present invention is to develop a method of treating a patient having a fungal infection, such as athlete's foot, by orally or topically administering an effective fungal infection treatment amount of valacyclovir hydrochloride or the like to said patient to eliminate the symptoms of fungal infection.

When taken orally, valacyclovir hydrochloride is preferably given to a patient in a daily amount of 0.05 to 4 grams for seven days, depending on the patient's body weight. The daily amount is preferably divided into three portions and administered every eight hours.

Another object of the present invention is to develop a method of treating a patient having a fungal infection, such as athlete's foot, by orally or topically administering an effective fungal infection treatment amount of an antiviral agent selected from the group consisting of acyclovir, valacyclovir, famciclovir, penciclovir and ganciclovir to said patient to eliminate the symptoms of said fungal infection.

The various features of novelty which characterize the invention are pointed out with particularity in the claims annexed to and forming a part of the disclosure. For a better understanding of the invention, its operating advantages, and specific objects attained by its use, reference should be had to the descriptive matter in which there are illustrated and described preferred embodiments of the invention.

DETAILED DESCRIPTION OF THE PRESENTLY PREFERRED EMBODIMENTS

As used herein, the term antiviral agent includes acyclovir (U.S. Pat. No. 4,199,574), valacyclovir (U.S. Pat. No. 4,957,924) and valacyclovir hydrochloride, famciclovir (U.S. Pat. No. 5,246,937) and the like. The properties of these antiviral agents are described in U.S. Pat. Nos. 4,199,574, 4,957,924, and 5,246,937, the contents of which are incorporated by reference in their entirety. All these antiviral agents are commercially available or can be readily obtained.

As used herein, the term "effective fungus infection treatment amount" means an amount that is capable of reducing, eliminating or otherwise improving the symptoms of the fungus infections, such as athlete's foot, or any amount that is apparent to or can be prescribed by a person of ordinary skill in the art without undue experimentation.

Fungal infections, including tineapedis (fungal infections on the feet), tineamanus (fungal infections on the hands) and tineacorporis (fungal infections on the body), are diagnosed by methods or tests commonly conducted by a person of ordinary skill in the art. The common symptoms of such disease are described above. In the case of fungal infection on nails such as finger nails and toenails, the infected areas usually show thickening of the nails with white spots, while if the skin is infected, itching scaling, redness and/or blisters will appear. A laboratory test may be conducted by culturing a skin sample or nail sample in the infected area in an appropriate medium to observe the growth of fungi. The infections may also be identified by scraping the infected skin or nail and examining the such specimen under a microscope in the presence of potassium hydroxide, which assists to determine the presence of fungi.

For the treatment of fungus infections, such as athlete's foot, the antiviral agents, such as acyclovir, valacyclovir, valacyclovir hydrochloride, famciclovir, or ganciclovir, may be administered parenterally or orally, or topically applied to the infected area as described below, or in accordance with the dosage regimens and administration routes described in any available editions of the Physician's Desk Reference or known to a person of ordinary skill in the art. When used topically, the amount of the drug applied depends on the size of the infected area and generally is the amount that can sufficiently cover such infected area. The treatment may begin at any stage of athlete's foot or the fungus infections, preferably as soon as possible after symptoms appear as can be determined by a person of ordinary skill in the art, and end until the symptoms of the infections begin to improve or no longer exist. The treatment may be repeated if there is recurrence of the symptoms.

The formulations for acyclovir, valacyclovir, famciclovir, penciclovir or ganciclovir include those suitable for oral or topical administrations. The formulations may be conveniently be presented in unit dosage form and may be prepared by any of the methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers of finely divided solid carriers or both, and then, if necessary, shaping the products.

For oral administration, acyclovir is calculated as the free base of about 0.05 to 250 mg per kilogram, preferably 0.5 to 50 mg per kilogram, of the patient's body weight, and are used in a unit dosage form, administered a few times daily in the amount of 0.5 to 250 milligram per unit dose.

Alternatively for infections of other external tissues, e.g. mouth and skin acyclovir is preferably applied to the infected part of the body of the patient as a topical ointment or cream. The compounds may be presented in an ointment, for instance with a water soluble ointment base, or in a cream, for instance with an oil in water cream base, in a concentration of from about 0.05 to 10%; preferably 0.05 to 7%, most preferably 0.5% w/v.

For each, oral and topical administration, a suitable dose of valacyclovir will be in the range 0.05 to 250 milligram per kilogram bodyweight of the patient per day, preferably in the range 0.05 to 100 milligram per kilogram bodyweight per day and most preferably in the range 2.5 to 20 milligrams per kilogram bodyweight per day; an optimum dose is about 10 milligram per kilogram bodyweight per day. The desired dose is preferably presented as two, three, four or more sub-doses administered at appropriate intervals throughout the day. These sub-doses may be administered in unit dosage forms, for example, containing 5 to 1000 milligram, preferably 10 to 500 milligram and most preferably 50 to 400 milligram of active ingredient per unit dosage form.

For infections of other external tissue, e.g. mouth and skin, the formulations of valacyclovir or its contraverse are preferably applied as a topical ointment or cream containing the active ingredient in an amount of, for example, 0.0325 to 20% w/w, preferably 0.1 to 15% w/w and most preferably 0.25 to 10% w/w. When formulated in an ointment, the active ingredients may be employed with either paraffinic or a water-miscible ointment base. Alternatively, the active ingredients may be formulated in a cream with an oil-in-water cream base. In addition topical applications may be made transdermally by means of an iontophoretic device.

Valacyclovir hydrochloride is preferably administered, orally, to patients suffering from athlete's foot or fungal infections. Such daily amount is preferably divided into three portions and to administered every eight hours. Thus, valacyclovir hydrochloride is preferably administered three times per day in a total daily amount of 0.05 to 4 grams, depending on patients' body weights and severity of infections. Normally a treatment period is seven days but may be extended if necessary. A preferred dosage for treating fungal infections is 750 mg to 1 gram orally 3 times daily for seven days. The dose may also be increased or decreased depending on the patients' physical conditions such as renal function, pregnancy and/or the immune system function, as can be determined by a person of ordinary skill in the art. Valacyclovir hydrochloride may also be applied topically to patients suffering from athlete's foot or fungus infections by applying a topical formulation, such as ointment, lotions, gel or the like containing the active ingredient valacyclovir hydrochloride in a concentration of at least 0.5% by weight, preferably about 1-10% by weight, to the infected area in an amount comparable to the topical formulations of other similar antiviral agents, as described in the present application.

Preferably, famciclovir is in unit dosage form or in some other form that the patient may take oneself. A suitable dosage unit might contain from 15 milligrams to 1 gram of active ingredient, for example 50 to 500 milligrams. Such doses may be administered 1 to 4 times a day or more usually 2 or 3 times a day. The effective dose of famciclovir will in general be in the range of from 0.5 to 10 milligrams per kilogram of body weight per day or more usually 1.0 to 10 milligrams per kilogram of body weight per day.

For oral administration, ganciclovir is calculated as the free base of about 0.05 to 250 mg per kilogram, preferably 0.5 to 50 mg per kilogram, of the patient's body weight, and are used in a unit dosage form, administered a few times daily in the amount of 0.5 to 250 milligram per unit dose.

For topical administration, penciclovir is preferably contained in a topical formulation in an amount about 10 mg per gram of the topical formulation. Preferably, the penciclovir topical formulation is applied about every two hours during the patient's waking hours for a period of about four days.

All the other aspects relating to the applications of acyclovir, valacyclovir, famciclovir and ganciclovir are specified in the U.S. Pat. Nos. 4,199,574, 4,957,924, and 5,246,937, respectively.

The following example serves to further illustrate the present invention and should not be construed as limitations to the scope of the present invention.

EXAMPLE

A male patient suffered from athlete's foot for four years. The patients toe nails had became whitening, thickening and cracking due to the infection. The skin of the patient's feet showed itching scaling. The patient was reported to experienced pain due to the thickening and cracking of the toe nails the swelling of the skin. The patient had been treated topically with 1% of butematine hydrochloride cream (Mentax) for about four years without success. After the treatment of butematine hydrochloride was stopped, the patient was given Valtrex (valacyclovir hydrochloride) at a daily dosage of three grams divided into three times for seven days (The patients body weight is about 230 pounds). At the end of treatment, the symptoms of the patient's athlete's foot completely disappear. The laboratory test also confirmed that there was no longer fungal infections on the patient's toe nails and the skin.

The invention is not limited by the embodiments described above which are presented as examples only but can be modified in various ways within the scope of protection defined by the appended patent claims.

Thus, while there have shown and described and pointed out fundamental novel features of the invention as applied to a preferred embodiment thereof, it will be understood that various omissions and substitutions and changes in the form and details of the examples illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

We claim:

1. A method of treating a patient having a fungal infection, comprising orally administering an effective fungal infection treatment amount of valacyclovir hydrochloride to said patient to eliminate the symptoms of said fungal infection; wherein said fungal infection is athlete's foot.

2. The method of claim 1, wherein said valacyclovir hydrochloride is administered for seven days in a daily amount of 0.05 to 4 grams.

3. The method of claim 2, wherein said daily amount of valacyclovir hydrochloride is administered three times per day.

4. The method of claim 3, wherein said daily amount of valacyclovir hydrochloride is administered 1 gram.

5. A method of treating a patient having a fungal infection, comprising topically administering an effective fungal infection treatment amount of a topical formulation of valacyclovir hydrochloride to the infected area of said patient to eliminate the symptoms of said fungal infection; wherein said fungal infection is athlete's foot.

6. The method of claim 5, wherein said topical formulation contains at least 0.5% of valacyclovir hydrochloride.

7. The method of claim 5, wherein said topical formulation contains about 1-10% of valacyclovir hydrochloride.

8. A method of treating a patient having a fungal infection, comprising orally administering an effective fungal infection treatment amount of an antiviral agent selected from the group consisting of acyclovir, valacyclovir, famciclovir, and ganciclovir to said patient to eliminate the symptoms of said fungal infection; wherein said fungal infection is athlete's foot.

9. A method of treating a patient having a fungal infection, comprising topically administering an effective fungal infection treatment amount of a topical formulation of an antiviral agent selected from the group consisting of acyclovir, valacyclovir, famciclovir, penciclovir and ganciclovir to the infected area of said patient to eliminate the symptoms of said fungal infection; wherein said fungal infection is athlete's foot.

* * * * *